United States Patent [19]

Prakash et al.

[11] Patent Number: 5,994,593
[45] Date of Patent: Nov. 30, 1999

[54] SYNTHESIS AND PURIFICATION OF 3,3-DIMETHYLBUTYRALDEHYDE VIA HYDROLYSIS OF 1,1-DICHLORO-3,3-DIMETHYLBUTANE OR 1-BROMO-1-CHLORO-3,3-DIMETHYLBUTANE

[75] Inventors: Indra Prakash, Hoffman Estates; Zhi Guo, Chicago, both of Ill.

[73] Assignee: The NutraSweet Company, Chicago, Ill.

[21] Appl. No.: 09/154,150

[22] Filed: Sep. 17, 1998

[51] Int. Cl.$^6$ .................................................. C07C 45/63
[52] U.S. Cl. ........................... 568/490; 568/449; 568/491
[58] Field of Search ................................... 568/450, 427, 568/449, 491, 490; 426/548

[56] References Cited

U.S. PATENT DOCUMENTS

| | | | |
|---|---|---|---|
| 5,480,668 | 1/1996 | Nofre | 426/548 |
| 5,510,508 | 4/1996 | Claude | 560/41 |
| 5,728,862 | 3/1998 | Prakash | 560/40 |

FOREIGN PATENT DOCUMENTS 721400  3/1980  U.S.S.R. .

OTHER PUBLICATIONS

Perrin et al, Purification of Laboratory Chemicals, 2nd edition, pp. 46–47, 67–68 and 553, 1980.
D.G. Botteron et al., "Syntheses of 2,5,5–trimethyl–3–hexanone, 2,5,5–trimethyl–2–hexanol, 2,3–epoxy–heptane, 2,3–heptanediol, and 4,4–dimethyl–1, 2–pentanediol", J. Org. Chem., vol. 27, pp. 1059–1061 (1962).
L. Schmerling, "Condensation of Saturated Halides with Unsaturated Compounds", J. Am. Chem. Soc., vol. 68, pp. 1650–1654 (1946).
D.D. Perrin et al., "Purification of Laboratory Chemicals", 3rd ed., Pergamon Press, New York, pp. 60–61 (1988).
A. Brandstrom, "A New Method to Prepare Trialkylacetic Acids", Acta Chem. Scand., vol. 13, No. 3, pp. 610–611 (1959).

*Primary Examiner*—Shailendra Kumar
*Assistant Examiner*—Sreeni Padmanabhan
*Attorney, Agent, or Firm*—Fitzpatric, Cella, Harper & Scinto

[57] ABSTRACT

3,3-Dimethylbutyraldehyde is synthesized via hydrolysis of 1,1-dichloro-3,3-dimethylbutane or 1-bromo-1-chloro-3,3-dimethylbutane in the presence of water and a base and is purified via an aldehyde/bisulfite adduct.

17 Claims, No Drawings

SYNTHESIS AND PURIFICATION OF 3,3-DIMETHYLBUTYRALDEHYDE VIA HYDROLYSIS OF 1,1-DICHLORO-3,3-DIMETHYLBUTANE OR 1-BROMO-1-CHLORO-3,3-DIMETHYLBUTANE

BACKGROUND OF THE INVENTION

1. Field of the Invention

This invention relates to the synthesis and purification of 3,3-dimethylbutyraldehyde via hydrolysis of 1,1-dichloro-3,3-dimethylbutane or 1-bromo-1-chloro-3,3-dimethylbutane with high purity.

2. Related Background Art

A method for synthesizing 3,3-dimethylbutyraldehyde via hydrolysis of 1,1-dichloro-3,3-dimethylbutane at 300° C. with a 60% yield is reported by L. Schmerling J. Am. Chem. Soc., vol. 68, 1946, pp. 1650–1654. This reaction would generate hydrochloric acid but was carried out in a closed system by heating a mixture of water and 1,1-dichloro-3,3-dimethylbutane without addition of a base. It is well known that hydrochloric acid is very corrosive to typical commercial reactors, which are constructed of metal alloys, especially at high temperature and pressure. Such reaction conditions are highly undesirable because they may lead to structural failure of the reactors and may be very hazardous.

A method for synthesizing 3,3-dimethylbutyraldehyde via hydrolysis of 1,1-dichloro-3,3-dimethylbutane at 180°–200° C. is disclosed in Soviet Patent No. 721400. The method disclosed therein comprises heating 1,1-dichloro-3,3-dimethylbutane with water in the presence of catalytic amounts of magnesium oxide or triethylamine, at 180°–200° C. The yield is reported to be 88–90%.

However, repetition of this reported reaction was found to give a significant amount (30–40%) of cis and trans tert-butyl vinyl chloride and 43% of the starting material remained unreacted. This is highly undesirable because the boiling points of 3,3-dimethylbutyraldehyde and tert-butyl vinyl chloride are very close; hence, they can not be separated by distillation techniques.

Purification of aldehydes by their conversion into a solid aldehyde/bisulfite adduct has been described in the literature. "Purification of Laboratory Chemicals" (Pergamon Press, 1988), pages 60–61, is incorporated by reference herein as a general reference for this methodology. Typically, the crude aldehyde is stirred with aqueous sodium bisulfite or sodium bisulfite in a mixture of water and alcohol. The precipitates are isolated, washed with water and/or alcohol, and then converted into free aldehyde with a base or acid.

3,3-Dimethylbutyraldehyde is an intermediate that is useful in the preparation of the sweetener N-[N-(3,3-dimethylbutyl)-L-α-aspartyl]-L-phenylalanine disclosed in U.S. Pat. No. 5,480,668, U.S. Pat. No. 5,510,508 and U.S. Pat. No. 5,728,862. Thus, despite the techniques for the hydrolysis of 1,1-dichloro-3,3-dimethylbutane described in the prior art, it is clear that there is a need to economically produce 3,3-dimethylbutyraldehyde using more efficient methods than currently available.

SUMMARY OF THE INVENTION

This invention is directed to the synthesis and purification of 3,3-dimethylbutyraldehyde with high purity. In particular, this invention is directed to a method for preparing 3,3-dimethylbutyraldehyde comprising the steps of heating 1,1-dichloro-3,3-dimethylbutane or 1-bromo-1-chloro-3,3-dimethylbutane in the presence of water and a base; mixing the resulting 3,3-dimethylbutyraldehyde with a first organic solvent and an aqueous solution of sodium bisulfite in order to form a bisulfite precipitate of the 3,3-dimethylbutyraldehyde; washing said bisulfite precipitate with a second organic solvent; and contacting, with heating, said washed bisulfite precipitate with an inorganic acid or base in order to yield purified 3,3-dimethylbutyraldehyde.

DETAILED DESCRIPTION

In the present invention, 3,3-dimethylbutyraldehyde is formed by the hydrolysis of 1,1-dichloro-3,3-dimethylbutane or 1-bromo-1-chloro-3,3-dimethylbutane in the presence of water and a base as illustrated below:

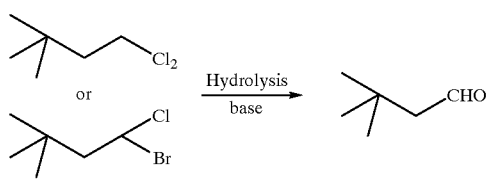

The aldehyde product prepared via the above-described embodiment of this invention is purified through an aldehyde/bisulfite adduct followed by the regeneration of the aldehyde as illustrated below:

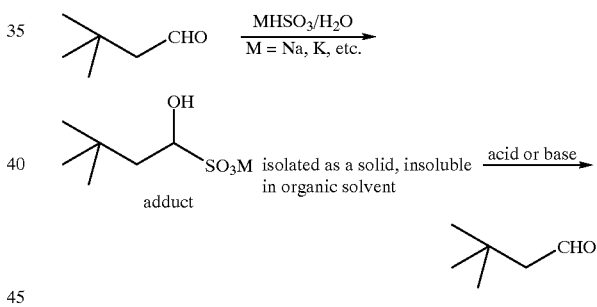

The 1,1-dichloro-3,3-dimethylbutane precursor is commercially available, e.g., from Aldrich Chemicals, Milwaukee, Wis. The 1-bromo-1-chloro-3,3-dimethylbutane precursor is formed by a method such as described by Arne Brandstrom, Acta Chem. Second, 13, 610 (1959). In the practice of this invention, the 1,1-dichloro-3,3-dimethylbutane or 1-bromo-1-chloro-3,3-dimethylbutane is then heated in the presence of water and a base.

The base is selected from an inorganic or an organic base. A mixture of bases is also effective. The inorganic base may preferably be selected from sodium bicarbonate, potassium bicarbonate, sodium carbonate, potassium carbonate, zinc oxide, aluminum oxide, zinc carbonate, magnesium oxide, calcium oxide, calcium carbonate, magnesium carbonate, potassium phosphates (monobasic, dibasic and tribasic), sodium phosphates (monobasic, dibasic and tribasic), ammonium phosphate, calcium phosphate, magnesium phosphate, ammonia or mixtures thereof. The organic base may preferably be a tertiary amine or a pyridine derivative.

Generally, the reaction time ranges from about 1 to about 48 hours. Preferably, the reaction time ranges from about 3 to about 24 hours. Most preferably, the reaction time ranges from about 4 to about 10 hours.

Generally, the reaction temperature ranges from about 170° C. to about 350° C. Preferably, the reaction temperature ranges from about 200° C. to about 300° C. Most preferably, the reaction temperature ranges from about 230° C. to about 280° C.

The aldehyde is collected and purified via its sodium bisulfite adduct using organic solvents. This purification preferably includes the following steps:

A. A mixture of the aldehyde product, a first organic solvent, and an aqueous sodium bisulfite solution is stirred for a period of time.

B. The solid adduct is isolated by filtration and the solid is washed thoroughly with a second organic solvent.

C. The solid adduct is dried.

D. 3,3-dimethylbutyraldehyde is regenerated by heating a mixture of the dried solid aldehyde/bisulfite adduct and an aqueous inorganic base or acid, followed by distillation.

The stirring time in Step A is generally from about 10 minutes to about 1440 minutes, preferably from about 20 minutes to 600 minutes, most preferably from 30 minutes to 360 minutes.

The first organic solvent in Step A is preferably an ether, a hydrocarbon compound, an ester, an alcohol or a mixture of the above. In another preferred embodiment of the present invention, the first organic solvent is the same as the second organic solvent in Step B.

The second organic solvent in Step B is any organic solvent in which the adduct is insoluble. The organic solvent may be water-miscible or water-immiscible. Preferably the organic solvent is isopropanol, MTBE, heptane, hexane, ethylacetate, cyclohexane, toluene, or a mixture thereof.

The inorganic acid or base in Step D is preferably hydrochloric acid, sulfuric acid, phosphoric acid, sodium bicarbonate, sodium carbonate, potassium bicarbonate, potassium carbonate, calcium carbonate, or mixtures thereof. In a preferred embodiment of the present invention, the inorganic base is a carbonate or bicarbonate.

The 3,3-dimethylbutyraldehyde produced and purified by the methods of this invention is sufficiently pure for use in the synthesis of highly pure N-[N-(3,3-dimethylbutyl)-L-α-aspartyl]L-phenylalanine 1 methyl ester (neotame).

The Examples which follow are intended as an illustration of certain preferred embodiments of the invention, and no limitation of the invention is implied.

EXAMPLE 1

Preparation of 3,3-dimethylbutyraldehyde by Hydrolysis of 1,1-dichloro-3,3-dimethylbutane with ZnO 30.0 g 1,1-dichloro-3,3-dimethylbutane, 15.0 g ZnO and 30.0 g water were loaded into a 150 ml Parr reactor. The reactor was sealed, stirred and heated at 250° C. for 7.5 hours. After the reactor was cooled to room temperature, the mixture was extracted with 100 ml methyl tert-butyl ether (MTBE), and the organic layer was separated. To this organic layer was added 10 g sodium bisulfide in 20 g water dropwise with agitation at 5° C., and the mixture was stirred for another 60 minutes before filtration. The solid was washed with 3×40 ml MTBE and dried in an 40° C. oven. Weight of the solid: 14.9 g.

The above solid, 7.3 g sodium bicarbonate and 70 g water were loaded into a round bottom flask and the mixture was heated to reflux. 3,3-Dimethylbutyraldehyde was distilled off from this mixture. Yield: 7.0 g.

Comparative Example 1

Preparation of 3,3-dimethylbutyraldehyde via Russian Patent 721400 Procedure 1,1-Dichloro-3,3-dimethylbutane (15 g), magnesium oxide (2 g), triethyl amine (3 g) and water (27 ml) were loaded into a Parr reactor. The reactor was sealed, stirred and heated at 200° C. for 4 hours. 1H NMR of the product showed 21% of 3,3-dimethylbutyraldehyde, 36% cis and trans tert-butyl vinyl chloride and 43% starting material.

Other variations and modifications of this invention will be obvious to those skilled in this art. This invention is not to be limited except as set forth in the following claims.

What is claimed is:

1. A method for preparing pure 3,3-dimethylbutyraldehyde comprising the step of:

heating 1,1-dichloro-3,3-dimethylbutane or 1-bromo-1-chloro-3,3-dimethylbutane in the presence of water and a weak base for a time and at a temperature sufficient to form 3,3-dimethylbutyraldehyde;

mixing the 3,3-dimethylbutyraldehyde with a first organic solvent and an aqueous solution of sodium bisulfite for a time sufficient to form a bisulfite precipitate of the 3,3-dimethylbutyraldehyde;

washing the bisulfite precipitate with a second organic solvent; and contacting, with heating, the washed bisulfite precipitate with an aqueous inorganic base or acid to yield purified 3,3-dimethylbutyraldehyde.

2. The method of claim 1, wherein the base is selected from the group consisting of sodium bicarbonate, potassium bicarbonate, zinc oxide, zinc carbonate, aluminum oxide, monobasic potassium phosphate, dibasic potassium phosphate, monobasis sodium phosphate, dibasic sodium phosphate, and mixtures thereof.

3. The method of claim 1 wherein the time sufficient to form 3,3-dimethylbutyraldehyde is from about 1 hour to about 48 hours.

4. The method of claim 3 wherein the time sufficient to form 3,3-dimethylbutyraldehyde is from about 3 hours to about 24 hours.

5. The method of claim 4 wherein the time sufficient to form 3,3-dimethylbutyraldehyde is from about 4 hours to about 10 hours.

6. The method of claim 1 wherein the temperature sufficient to form 3,3-dimethylbutyraldehyde is from about 170° C. to about 350° C.

7. The method of claim 6 wherein the temperature sufficient to form 3,3-dimethylbutyraldehyde is from about 200° C. to about 300° C.

8. The method of claim 7 wherein the temperature sufficient to form 3,3-dimethylbutyraldehyde is from about 230° C. to about 280° C.

9. The method of claim 1, wherein the first organic solvent is the same as the second organic solvent.

10. The method of claim 1, wherein the first organic solvent is an ether, a hydrocarbon, an ester, an alcohol or a mixture thereof, and the second organic solvent is an ether, a hydrocarbon, an ester, an alcohol or a mixture thereof.

11. The method of claim 1, wherein the time sufficient to form a bisulfite precipitate is from about 10 minutes to about 1440 minutes.

12. The method of claim 11, wherein the time sufficient to form a bisulfite precipitate is from about 20 minutes to about 600 minutes.

13. The method of claim 12, wherein the time sufficient to form a bisulfite precipitate is from about 30 minutes to about 360 minutes.

14. The method of claim 1, wherein the second organic solvent is selected from the group consisting of isopropanol, methyl tert-butyl ether, heptane, hexane, ethylacetate, cyclohexane, toluene, and mixtures thereof.

15. The method of claim 1, wherein the aqueous inorganic base or acid is selected from the group consisting of hydrochloric acid, sulfuric acid, phosphoric acid, sodium bicarbonate, sodium carbonate, potassium bicarbonate, potassium carbonate, calcium carbonate and mixtures thereof.

16. The method of claim 1, wherein the aqueous inorganic base is a carbonate or a bicarbonate.

17. The method of claim 1, wherein the base is zinc oxide.

\* \* \* \* \*

UNITED STATES PATENT AND TRADEMARK OFFICE
CERTIFICATE OF CORRECTION

PATENT NO. : 5,994,593

DATED : November 30, 1999

INVENTOR(S) : INDRA PRAKASH ET AL.

It is certified that error appears in the above-identified patent and that said Letters Patent is hereby corrected as shown below:

On the title page, item [56], References Cited, in OTHER PUBLICATIONS, after *Attorney, Agent, or Firm* - "Fitzpatric, Cella, Harper & Scinto" should read --Fitzpatrick, Cella, Harper & Scinto--.

COLUMN 1

Line 16, "J.Am." should read --in J.Am.--.

COLUMN 4

Line 1, "an" should read --a--;
Line 22, "step" should read --steps--; and
Line 41, "monobasis" should read --monobasic--.

Signed and Sealed this

Twenty-third Day of January, 2001

Attest:

Attesting Officer

Q. TODD DICKINSON

Commissioner of Patents and Trademarks